United States Patent [19]

McDonald

[11] 4,333,952
[45] Jun. 8, 1982

[54] GROWTH PROMOTORS FOR RUMINANTS

[75] Inventor: Brian G. McDonald, Mosspark, Scotland

[73] Assignee: Beecham Group Limited, England

[21] Appl. No.: 164,085

[22] Filed: Jun. 30, 1980

[30] Foreign Application Priority Data

Jul. 10, 1979 [GB] United Kingdom ............... 7924026
Dec. 1, 1979 [GB] United Kingdom ............... 7941534

[51] Int. Cl.³ ............... A61K 31/085; A61K 31/12;
A61K 31/135; A61K 31/045
[52] U.S. Cl. .................. 424/330; 424/331;
424/341; 424/343; 568/648; 568/305; 568/335;
568/336; 568/644; 568/649; 568/339; 568/811;
568/442; 568/307; 568/662; 564/442
[58] Field of Search ........... 568/644, 649, 335, 336,
568/337, 811, 812; 564/442, 305, 307; 424/340,
330, 331, 343, 341

[56] References Cited

U.S. PATENT DOCUMENTS

| | | | |
|---|---|---|---|
| 2,150,001 | 3/1939 | Lange | 564/442 |
| 2,489,935 | 11/1949 | Searle | 424/340 |
| 2,659,757 | 11/1953 | Druey | 568/335 |
| 2,700,686 | 1/1955 | Dickey et al. | 564/442 |
| 3,101,345 | 8/1963 | Schmidt | 568/649 |
| 3,183,147 | 5/1965 | Homeyer et al. | 424/340 |
| 3,595,882 | 7/1971 | Bremmer | 564/442 |
| 3,627,847 | 12/1971 | Langkammerer | 568/811 |
| 3,637,852 | 1/1972 | Koppe et al. | 568/649 |
| 3,894,075 | 7/1975 | Grandadam | 424/340 |
| 4,140,794 | 2/1979 | Piccardi et al. | 568/337 |

FOREIGN PATENT DOCUMENTS

49-124005 8/1974 Japan ................... 568/337
1123845 8/1968 United Kingdom ........ 568/811

OTHER PUBLICATIONS

Ried et al., Chem. Ber., vol. 100, pp. 605-610 (1967).

*Primary Examiner*—Natalie Trousof
*Assistant Examiner*—James H. Reamer
*Attorney, Agent, or Firm*—Jacobs & Jacobs

[57] ABSTRACT

Compounds of formula (I):

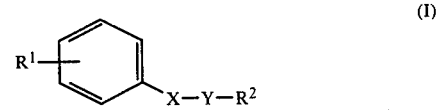

wherein:
$R^1$ is hydrogen, halogen or $C_{1-4}$ alkoxy;
X is oxygen; $NR^3$ in which $R^3$ is hydrogen, $C_{1-4}$ alkyl, or $-Y-R^2$; $-C=O$; or $-CHOH$;
Y is $-CH_2-CHOH$, and when X is $-C=O$ it may also be $-CH=CH-$; and
$R^2$ is $C_{1-4}$ alkyl, one carbon atom of which is di- or tri-halogenated;

or salts thereof, are useful in promoting growth of ruminants. Processes for their production, veterinary formulations and treatments are described.

25 Claims, No Drawings

GROWTH PROMOTORS FOR RUMINANTS

This invention relates to compounds having the ability to promote growth in ruminant animals, to compositions containing these compounds, and to a method for the preparation of these compounds.

U.S. Pat. No. 4,112,091 discloses a class of compounds of formula (A) below, precisely substituted piperazines:

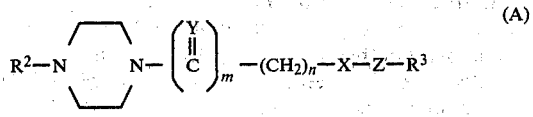

wherein $R^2$ is hydrogen, lower alkyl, lower hydroxyalkyl or phenyl optionally substituted with one lower alkyl or hydroxyalkyl group; Y is oxygen or sulphur; X is a group of formula $<\!C\!=\!O$, $<\!C\!=\!S$ or —CHOH; Z is oxygen, sulphur or a direct bond; $R^3$ is a straight- or branched-chain alkyl or alkenyl group, which is substituted at one methyl group by two or three halogen atoms, or is an adamantyl group; m is 0 or 1; and n is an integer from 0 to 4, provided that when m=0 then n=0; with the proviso that, when X is a group of formula —CHOH—, then m is 0, n is 1 and Z is a direct bond.

West German Offenlegungsschrift No. 2,553,021 discloses that a class of compounds of formula (B) below, precisely substituted 5-nitroimidazoles;

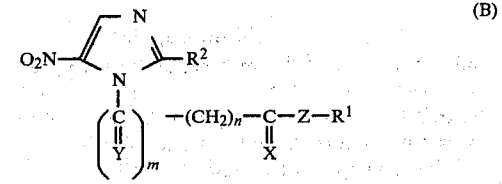

wherein $R^1$ is straight-chain or branched-chain alkyl or alkenyl optionally mono-substituted by phenyl or in which one methyl group is replaced by a mono-, di-, or trihalo-methyl group or $R^1$ is adamantyl or a phenyl optionally mono- or poly-substituted by $NO_2$, lower alkyl, lower alkoxy, halogen or $CF_3$; $R^2$ is H or lower alkyl; X, Y and Z are the same or different O or S; n is 0, 1, 2, 3 or 4; and m is 0 or 1; provided that when m is 0, X and Z are both O, n is 1–4 and $R^2$ is H or $CH_3$, then $R^1$ is other than benzyl, unsubstituted alkyl, or phenyl.

British Pat. No. 1123845 discloses a class of phenoxy-trichloropropanols of the formula (C) below

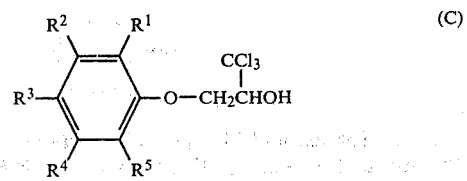

in which $R^1$, $R^2$, $R^3$, $R^4$ and $R^5$ are each hydrogen, $C_1$ to $C_4$ alkyl, $C_1$ to $C_4$ alkoxy, halogen, carboxyl or nitrile and can be the same or different.

The compounds of formula (A) and (B) are stated to be useful feed additives for animals, especially ruminants, by virtue of their ability to inhibit methane formation and/or to displace fatty acid formation in favour of propionate formation.

The compounds of formula (C) are stated to be useful as rubber chemicals, lubricant additives, flame-retardant additives for polymers, and agricultural chemicals.

It has now been discovered that a narrow class of novel compounds structurally distinct from the compounds of formulae (A) and (B) may be used as feed additives for ruminants to enhance their growth.

Accordingly, the present invention provides a compound of the formula (I):

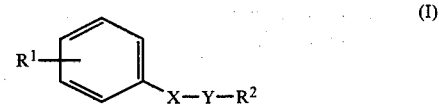

wherein:

$R^1$ is hydrogen, halogen or $C_{1-4}$ alkoxy;

X is oxygen; $NR^3$ in which $R^3$ is hydrogen, $C_{1-4}$ alkyl, or $—Y—R^2$; $—C\!=\!O$; or —CHOH—;

Y is $—CH_2—CHOH—$, and when X is $—C\!=\!O$ it may also be $—CH\!=\!CH—$; and $R^2$ is $C_{1-4}$ alkyl, one carbon atom of which is di- or tri-halogenated;

and salts thereof, for use in the treatment of the human or animal body.

Those compounds of formula (I) which are structurally distinct from the compounds of formula (C) are novel compounds.

Accordingly, the present invention further provides a novel compound of the formula (I) and salts thereof, with the proviso that X, Y and $R^2$ are not simultaneously oxygen, $—CH_2—CHOH—$, and $CCl_3$ respectively.

Suitable examples of $R^1$ include hydrogen, chloro, bromo and methoxy.

Suitable examples of X when $NR^3$ include NH, $NCH_3$ and $N—CH_2CHOHCCl_3$.

Suitable examples of $R^2$ include chlorinated methyl or ethyl groups, such as tri-chloromethyl and 2,2,2-trichloroethyl.

Salts of compounds of the formula (I) include acid addition salts with acids such as hydrochloric acid.

From the above it will be realised that one particularly suitable group of compounds within formula (I) is of formula (I)':

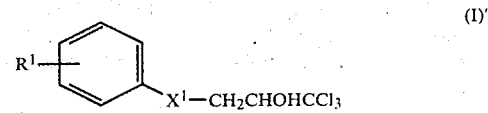

wherein $X^1$ is $NR^4$, wherein $R^4$ is hydrogen, methyl or $—CH_2CHOHCCl_3$; and R is as defined.

In formula (I)', preferably $R^1$ is hydrogen and $X^1$ is NH.

Another particularly suitable class of compounds are of formula (I)'':

wherein $X^2$ is —C=O or —CHOH, and Y and $R^1$ are as defined.

The invention also provides a process for the preparation of the compounds of the formula (I), which process comprises either:

(i) reacting a compound of the formula (II):

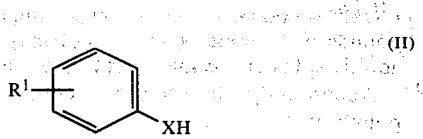

wherein X is oxygen or $NR^3$ with a compound of formula (III):

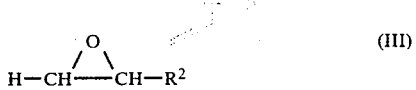

to yield a corresponding compound of the formula (I) wherein X is oxygen or $NR^3$ and Y is —CH$_2$—CHOH—; or (ii) reacting a compound of formula (IV):

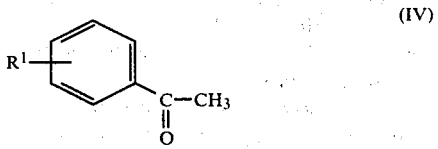

with a compound of $R^2$CHO, to yield a compound of formula (I) wherein X is —C=O and Y is —CH$_2$—CHOH—, and thereafter if necessary reducing such a compound to the corresponding X is —CHOH compound, or dehydrating such a compound to the corresponding Y is —CH=CH— compound.

The reaction (i) may suitably be carried out by dissolving the reactants in suitable organic solvents such as pyridine or ethyl acetate, and letting the reactants react together for a prolonged period. Often the reaction will go satisfactorily at room temperature, but on occasions if may be necessary or desirable to carry out the reaction under reflux.

The reaction (ii) is suitably carried out with heat and in the presence of a base, such as sodium carbonate.

Any subsequent reduction can be carried out in conventional manner, for example with sodium borohydride. Any subsequent dehydration can be carried out in the usual manner, for example by heating in the presence of an acid catalyst, such as p-toluene sulphonic acid.

The salts of compounds of the formula (I) can be prepared in the usual manner, for example by reacting a free base compound of the formula (I) with an acid.

Preferably the salt formed will be pharmaceutically acceptable.

The compounds of the formula (I) are useful food additives for ruminants, as they act as growth promotors by virtue of reduced or inhibited methane production and enhanced propionate production.

Accordingly, an important aspect of this invention lies in a veterinary composition comprising a compound of the formula (I) and a veterinarily acceptable carrier.

The carrier may obviously be a food stuff in which case conveniently the composition can be formed in situ by addition of the compound of the formula (I) to the animal feed.

Alternatively, the compound of the formula (I) may be administered to the animal separately from the feed, in which case the said veterinary composition will be a tablet, capsule, bolus, aqueous solution (which may be added to the drinking water) and the like. Such compositions may be formulated in conventional manner. Slow release formulations may also be used.

Clearly the active dose of the compound of the formula (I) will vary from compound to compound, and with the weight and nature of the ruminant concerned. However, by way of illustration, it is believed a level of compound in the diet of 1 to 1000 ppm, more suitably 1 to 200 ppm, will enable the beneficial effects of the compound to be obtained.

The following Examples illustrate the preparation of compounds of the formula (I) and their activity in an in vitro test system.

EXAMPLE 1

1,1,1-Trichloro-3-phenoxypropan-2-ol

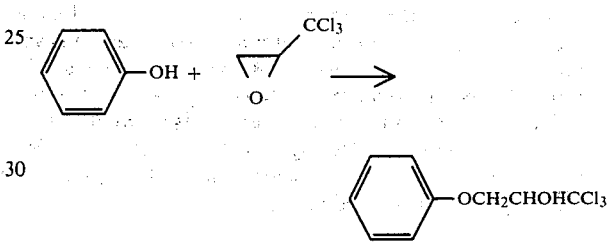

Phenol (25 g), trichloropropylene epoxide (50 ml) and pyridine (0.5 ml) were heated and stirred together at 90°–100° C. for 6 hours. The reaction mixture was then allowed to stand at room temperature overnight, and then vacuum distilled. Excess reagent was first distilled, followed by product at 105°–115° C./0.1 mm. The product solidified on standing and was crystallized from petrol ether (40–60) to give white crystals m.pt 54°–56° C.

$C_9H_9O_2Cl_3$: Requires: C, 42.27; H, 3.52. Found: C, 41.85; H, 3.45.

EXAMPLE 2

1,1,1-Trichloro-3-p-chlorophenoxypropan-2-ol

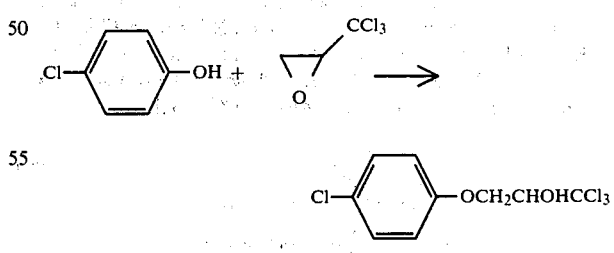

p-Chlorophenol (3.14 g), trichloropropylene epoxide (9.0 ml) and pyridine (0.1 ml) were heated and stirred together at 90°–100° C. for 6 hours. The reaction mixture was then distilled under vacuum to give the product, b.pt 120°–124° C./0.1 mm, yield 2.5 g. Crystallization from cyclohexane gave the product as a white solid, m.pt 47° C.

$C_9H_8O_2Cl_4$: Requires: C, 37.24; H, 2.76; Cl, 48.97. Found: C, 37.02; H, 2.98; Cl, 49.96.

EXAMPLE 3

1,1,1-Trichloro-3-o-bromophenoxypropan-2-ol

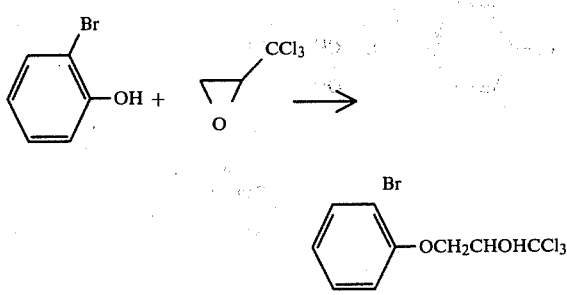

o-Bromophenol (4.0 g), trichloropropylene epoxide (4.0 g) and pyridine (0.1 ml) were stirred in ethyl acetate (10 ml) at room temperature for 3 days. The solution was filtered and vacuum distilled. The fraction boiling at 40° C./0.1 mm was first collected and discarded. The further fraction could be distilled over. The distillation was terminated and the solid material which had condensed on the distillation head and thermometer was scraped off (0.5 g). Re-crystallization from cyclohexane gave a white solid, m.pt. 88°–90° C.

$C_9H_8O_2Cl_3Br$: Requires: C, 32.30; H, 2.39; Cl, 31.85. Found: C, 33.91; H, 2.64; Cl, 30.64.

EXAMPLE 4

1,1,1-Trichloro-3-anilinopropan-2-ol

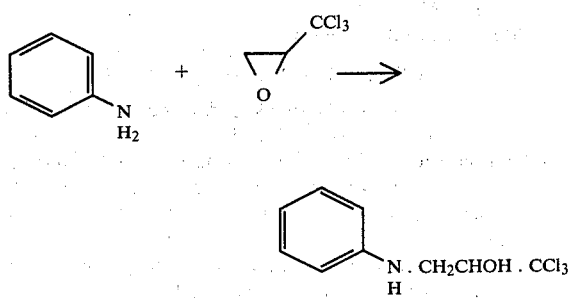

Aniline (1.9 ml) and trichloropropylene epoxide (2.2 ml) were stirred together in ethyl acetate (25 ml) under reflux for 8 hours. The solvent was evaporated and the solid residue crystallized from cyclohexane to give the product as white fluffy needles m.pt 114°–115° C., yield 3.31 g.

$C_9H_{10}NOCl_3$: Requires: C, 42.44; H, 3.93; N, 5.50; Cl, 41.85. Found: C, 42.47; H, 3.82; N, 5.40; Cl, 41.88.

EXAMPLE 5

1,1,1-Trichloro-3-N-methylanilinopropan-2-ol

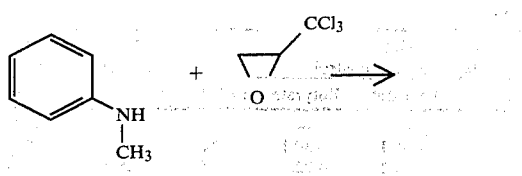

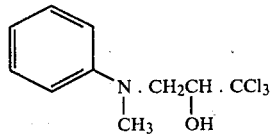

N-methylaniline (2.2 ml) and trichloropropylene epoxide (2.2 ml) were stirred and refluxed together in ethyl acetate (20 ml) for 5 hours. The solution was evaporated and the product crystallized from cyclohexane to give a white solid, m.pt 78°–80° C., yield 1.4 g.

$C_{10}H_{12}NOCl_3$: Requires: C, 44.69; H, 4.47; N, 5.21; Cl, 39.66. Found: C, 44.78; H, 4.54; N, 5.22; Cl, 40.05.

EXAMPLE 6

1,1,1-Trichloro-3-(m-methoxy)anilinopropan-2-ol

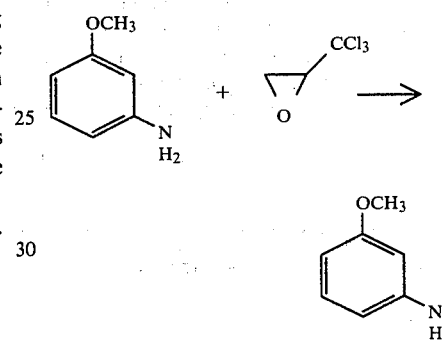

m-Anisidine (2.46 g) and trichloropropylene epoxide (2.2 ml) were refluxed together in ethyl acetate for 7 hours. The solution was evaporated on a rotary evaporator and the product crystallized from benzene to yield white crystals, m.pt 110°–112° C., yield 2.70 g.

$C_{10}H_{12}NO_2Cl_3$: Requires: C, 42.18; H, 4.22; N, 4.92; Cl, 37.43. Found: C, 42.22; H, 4.12; N, 4.83; Cl, 37.83.

EXAMPLE 7

N,N-Di (3,3,3-Trichloro-2-hydroxypropyl)aniline

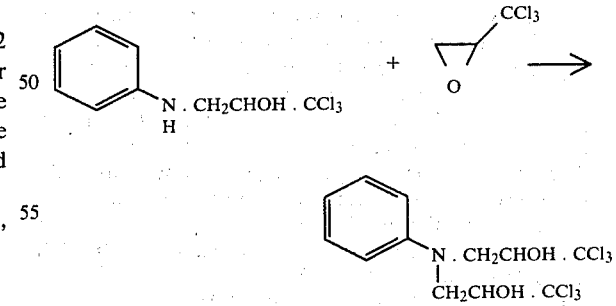

1,1,1-Trichloro-3-anilinopropan-2-ol (2.3 g) and trichloropropylene epoxide (10 ml) were stirred together at about 60° C. for 6 hours, then at room temperature overnight. The product was then filtered off, washed with petrol (yield 0.91 g) and crystallized from cyclohexane to give a white solid product, m.pt 149°–151° C.

$C_{12}H_{13}NO_2Cl_6$: Requires: C, 34.62; H, 3.13; N, 3.37; Cl, 51.20. Found: C, 35.07; H, 3.22; N, 3.30; Cl, 50.94.

EXAMPLE 8

1-p-Chlorophenacyl-2-hydroxy-3-trichloropropane

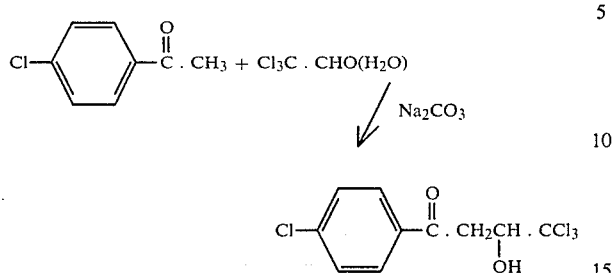

p-Chloroacetophenone (5.0 g) and chloral hydrate (5.0 g) were heated together neat with anhydrous sodium carbonate (1.0 g) at about 80° C. for five hours. The solution was allowed to cool and treated with chloroform and water. The layers were separated and the chloroform extract washed with water and dried over sodium sulphate. The solution was evaporated and the crude product recrystallized from benzene-petrol (60–80) to give white needles (2.05 g; m.pt 116°–118° C.).

$C_{10}H_8O_2Cl_4$: Requires C, 39.74; H, 2.65; Cl, 47.02. Found C, 39.68; H, 2.75; Cl, 47.32.

EXAMPLE 9

1-p-Chlorophenyl-1,3-dihydroxy-4,4,4-trichlorobutane

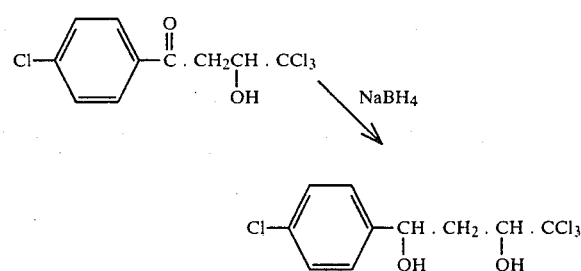

1-p-Chlorophenacyl-2-hydroxy-3,3,3-trichloropropan (600 mg) was dissolved in dioxan (10 ml) and treated with sodium borohydride (25 mg). The reaction mixture was stirred at room temperature for two hours and then a second portion of sodium borohydride (25 mg) added and the reaction mixture stirred overnight. The reaction mixture was quenched with dilute sulphuric acid and extracted with chloroform. The chloroform layer was washed with water and dried over sodium sulphate. On reduction of the volume of the chloroform solution and addition of petrol the product precipitated from the solution. This was collected by filtration and re-crystallized from benzene-petrol (60–80). Yield 350 mgs, m.pt 135°–137° C.

$C_{10}H_{10}O_2Cl_4$: Requires: C, 39.47; H, 3.29; Cl, 46.71. Found: C, 39.49; H, 2.81; Cl, 48.08.

EXAMPLE 10

1-p-Chlorophenacyl-3,3,3-trichloro-prop-1-ene

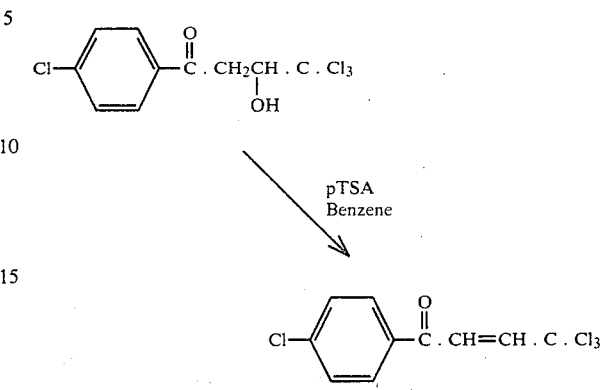

1-p-Chlorophenacyl-2-hydroxy-3,3,3-trichloropropane (450 mg) was dissolved in benzene and p-toluene sulphonic acid monohydrate (40 mg) added. The solution was refluxed with a Dean and Stark apparatus and any reaction followed by tlc. After 5 hours refluxing tlc revealed that only starting material was present. The solution was treated with a second portion of p-toluene sulphonic acid (100 mg) and further refluxed for 5 hours. The solution was allowed to stand over 60 hours and evaporated to dryness. tlc Analysis (10% Et.AC.-/petrol) revealed a new product (Rf 0.8) with no starting material remaining. The solution was taken up in ethyl acetate and passed down a short alumina column (to remove pTSA). Elution with 25% Et.Ac./petrol yielded the product. Yield 200 mg.

IR + NMR confirm.

Melting point 114°–116° C.

IN VITRO TEST DATA SECTION

The compounds were tested for their ability to reduce or inhibit methane production and to enhance propionate formation. The method used is as follows:

The screening system is in vitro incubation of buffered rumen fluid with, or without, the addition of the test compound.

Rumen fluid is removed by suction from two rumen-fistulated sheep, just before feeding. The fluid is strained and mixed. The incubation is for twenty hours in a shaking water-bath at 39° C. Each incubation flask contains: 30 ml McDougall's bicarbonate buffer, pH 6.7–6.9, 10 ml strained rumen fluid, 200 mg substrate (the substrate is a ground sample of the diet on which the sheep has been fed) and 1 ml 10% aqueous ethanol containing 0.2% Tween 80 and the compound under examination. Samples are taken at the end of the incubation period for analysis of headspace gases and volatile fatty acids, by g.l.c.

The compounds were tested at 10 ppm/flask, except for the compounds of Examples 9 and 10 which were tested at 5 ppm/flask.

The results obtained are shown in Table 1.

TABLE 1

| Compound of Example | Molar % VFA | | | μM/ml TVFA | VFA production % difference from control | | | | % inhibition of methane | % hydrogen present |
|---|---|---|---|---|---|---|---|---|---|---|
| | Acetate | Propionate | Butyrate | | Acetate | Propionate | Butyrate | TVFA | | |
| Control | 70.3 | 15.5 | 10.9 | 64.6 | — | — | — | — | — | 0.02 |
| 1 | 59.3 | 23.6 | 14.1 | 59.0 | −32.9 | +56.4 | +30.1 | −12.6 | 98.5 | 2.81 |
| 2 | 58.5 | 24.1 | 14.1 | 56.9 | −38.5 | +53.2 | +22.7 | −17.5 | 98.5 | 2.49 |

TABLE 1-continued

| Compound of Example | Molar % VFA | | | µM/ml TVFA | VFA production % difference from control | | | | % inhibition of methane | % hydrogen present |
|---|---|---|---|---|---|---|---|---|---|---|
| | Acetate | Propionate | Butyrate | TVFA | Acetate | Propionate | Butyrate | TVFA | | |
| 3 | 59.1 | 24.1 | 14.2 | 57.2 | −36.8 | +54.3 | +25.0 | −16.7 | 97.8 | 2.30 |
| 4 | 59.3 | 23.9 | 13.7 | 57.2 | −36.4 | +52.8 | +18.2 | −16.7 | 98.5 | 2.13 |
| 5 | 59.1 | 24.0 | 14.0 | 57.5 | −36.3 | +54.6 | +23.9 | −16.1 | 92.7 | 1.9 |
| Control | 73.9 | 15.78 | 7.16 | 68.3 | — | — | — | — | — | 0.003 |
| 6 | 63.2 | 24.9 | 8.50 | 55.4 | −40.4 | +36.8 | −6.6 | −25.3 | 97.5 | 2.59 |
| 7 | 61.9 | 24.8 | 9.72 | 56.2 | −40.8 | +39.0 | +18.9 | −24.7 | 87.9 | 2.17 |
| Control | 71.0 | 18.2 | 7.9 | 52.5 | — | — | — | — | — | 0.00 |
| 8 | 63.5 | 23.7 | 9.8 | 50.5 | −23.1 | +42.4 | +50.7 | −6.5 | 34.1 | 0.05 |
| 9 | 59.9 | 26.4 | 10.7 | 47.7 | −38.5 | +53.2 | +59.7 | −15.5 | 50.7 | 0.64 |
| 10 | 68.4 | 20.1 | 8.7 | 53.4 | −3.5 | +20.6 | +31.3 | +2.8 | 4.2 | 0.03 |
| A | 65.3 | 21.9 | 9.13 | 56.7 | −35.0 | +19.9 | +9.0 | −22.6 | 50.6 | 0.062 |

These results show the ability of the compounds of the invention to reduce methane formation and to enhance propionate formation.

Compound A in the Table is the compound of formula:

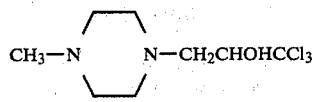

$$CH_3-N \bigcirc N-CH_2CHOHCCl_3$$

which is the compound of Example 11 of U.S. Pat. No. 4,112,091, and which is stated in the patent at column 3, lines 55 to 58 to be one of the two 'most preferred compounds'. It is interesting to note that in the initial tests reported in the Table the compounds of the Examples are generally approximately twice as active propionate enhancers, and approximately twice as active methane inhibitors, as this Compound A.

Selected compounds were also tested according to the above protocol at doses of 2 and 3 ppm, the results being given in Table 2 below.

TABLE 2

| Compound of Example | Dose Level ppm | VFA production % change from control | | | | % inhibition of methane | % hydrogen in headspace gases |
|---|---|---|---|---|---|---|---|
| | | Acetate | Propionate | Butyrate | TVFA | | |
| 2 | 2 | −22.6 | +25.2 | +2.0 | −11.5 | 33.3 | 0.09 |
| | 3 | −39.0 | +28.4 | +10.2 | −22.7 | 54.5 | 0.8 |
| 3 | 2 | −9.1 | +11.1 | +3.4 | −4.5 | 17.8 | 0.02 |
| | 3 | −35.5 | +43.1 | +26.8 | −15.6 | 54.7 | 0.66 |
| 4 | 2 | −12.8 | +27.2 | +3.0 | −4.0 | 20.8 | 0.09 |
| 5 | 2 | −4.3 | +0.8 | +0.8 | −3.1 | 4.2 | 0.02 |
| 6 | 2 | −9.3 | +12.6 | +15.3 | −4.5 | 11.5 | 0.03 |
| | 3 | −41.8 | +41.7 | +15.2 | −21.5 | 77.8 | 1.09 |

The compound of Example 1 was further tested in an in vitro a dose response study, according to the protocol above, at the doses shown in Table 3 below.

TABLE 3

| Dose Level ppm | VFA production % change from control | | | | % inhibition of methane | % hydrogen in headspace gases |
|---|---|---|---|---|---|---|
| | Acetate | Propionate | Butyrate | TVFA | | |
| 10 | −32.9 | +56.4 | +30.1 | −12.6 | 98.5 | 2.82 |
| 5 | −35.7 | +50.0 | +28.3 | −12.5 | 96.6 | 1.48 |
| 3 | −34.6 | +38.4 | +20.0 | −24.5 | 76.0 | 1.08 |
| 1.5 | −32.5 | +30.7 | +17.3 | −16.6 | 55.1 | 0.95 |
| 1.0 | −31.5 | +14.3 | +2.9 | −18.9 | 36.4 | 0.11 |
| 0.5 | −12.8 | +1.9 | −2.0 | −8.8 | 14.5 | 0.01 |

IN VIVO TEST DATA SECTION

In vivo studies in a "gas collection screen":

Groups of 4, 50 kg sheep were fed diets containing one of the compounds of formula (I) over a 5 week period. A different sheep from each group was put into a respirometer for 24 hours each day. Each sheep was thus monitored once in every 5 days, gas flow was maintained by a peristaltic pump and measured using a commercial gas meter and a sub-sample collected in a butyl-rubber inner tube. Gas analysis was carried out by gas chromatography using a R/E 204 gas chromatograph with both electron capture and flame ionisation detectors. During a run-in control period it was found that the sheep produced 19.2+0.4 liters methane/day and not more than 1.5 liters hydrogen/day.

The compounds were stable in the feed over the period of the study. By feeding measured amounts to the sheep (no refusals) it was possible to "dose" each sheep with 75 mg/day of each of the compounds.

The results for the 5 week period are given in Table 4 below:

TABLE 4

| Compound of Example | % inhibition of methanogenesis | Hydrogen evolution liters/24 hours |
|---|---|---|
| 1 | 41.2* | 5.6 |
| 4 | 11.5 | 1.8 |

*Significantly different from control methanogenesis level (p <0.01 students t test).

For the purposes of comparison, Monensin at 50 mg/sheep/day caused 41% methane inhibition in the same study over a 5 week period.

I claim:

1. The method of promoting growth in ruminants by inhibiting methane production and enhancing proprionate production which comprises orally administering to a ruminant an effective nontoxic amount of a compound of the formula:

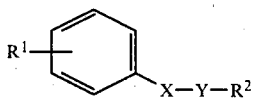

or a pharmaceutically acceptable salt thereof wherein
$R^1$ is hydrogen, halo or alkoxy of 1 to 4 carbon atoms;
X is oxygen, carbonyl, hydroxymethylene or $NR^3$ in which $R^3$ is hydrogen, alkyl of 1 to 4 carbon atoms or $-YR^2$,
Y is —CH$_2$CHOH— or, provided X is carbonyl, —CH=CH; and
$R^2$ is alkyl of 1 to 4 carbon atoms, one carbon atom of which is di- or trihalogenated.

2. A non-toxic veterinary composition for promoting the growth of ruminants, comprising a growth-promoting effective amount of a compound of the formula:

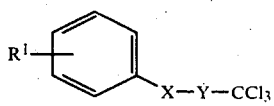

wherein $R^1$ is hydrogen, halo or alkoxy of 1 to 4 carbon atoms, X is oxygen, carbonyl, hydroxymethylene, imino, N-alkylimino wherein alkyl contains 1 to 4 carbon atoms or N-(3,3,3,-trichloro-2-hydroxypropyl)-imino; and Y is —CH$_2$CH(OH)— or, if X is carbonyl, Y is —CH$_2$CH(OH)— or ethylene, or a salt thereof, in combination with a food stuff for the ruminant, said compound being present in said food stuff in an amount of from 1 to 1000 ppm.

3. The method according to claim 1 wherein in said compound
$R^1$ is hydrogen, chloro, bromo or methoxy;
X is oxygen, imino, N-methylamino or N-(3,3,3-trichloro-2-hydroxypropyl)-imino;
Y is —CH$_2$CH(OH)—, and
$R^2$ is trichloromethyl.

4. The method according to claim 3 wherein in said compound X is oxygen.

5. The method according to claim 3 wherein in said compound X is imino, N-methylimino or N-(3,3,3-trichloro-2-hydroxypropyl)-imino.

6. The method according to claim 22 wherein said compound is 1,1,1-trichloro-3-phenoxypropan-2-ol.

7. A composition according to claim 2 wherein said compound is 1,1,1-trichloro-3-phenoxypropan-2-ol.

8. The method according to claim 1, wherein said compound is 1,1,1-trichloro-3-p-chlorophenoxypropan-2-ol.

9. The method according to claim 1, wherein said compound is 1,1,1-trichloro-3-o-bromophenoxypropan-2-ol.

10. The method according to claim 1, wherein said compound is 1,1,1-trichloro-3-anilinopropan-2-ol.

11. The method according to claim 1, wherein said compound is 1,1,1-trichloro-3-N-methylanilinopropan-2-ol.

12. The method according to claim 1, wherein said compound is 1,1,1-trichloro-3-(m-methoxy)anilinopropan-2-ol.

13. The method according to claim 1, wherein said compound is N,N-di-(3,3,3-trichloro-2-hydroxypropyl)-aniline.

14. The method according to claim 1, wherein said compound is 1-p-chlorophenacyl-2-hydroxy-3-trichloropropane.

15. The method according to claim 1, wherein said compound is 1-p-chlorophenyl-1,3-dihydroxy-4,4,4-trichlorobutane.

16. The method according to claim 1, wherein the compound is 1-p-chlorophenacyl-3,3,3-trichloroprop-1-ene.

17. The composition according to claim 2, wherein said compound is 1,1,1-trichloro-3-p-chlorophenoxypropan-2-ol.

18. The composition according to claim 2, wherein said compound is 1,1,1-trichloro-3-o-bromophenoxypropan-2-ol.

19. The composition according to claim 2, wherein said compound is 1,1,1-trichloro-3-anilinopropan-2-ol.

20. The composition according to claim 2, wherein said compound is 1,1,1-trichloro-3-N-methylanilinopropan-2-ol.

21. The composition according to claim 2, wherein said compound is 1,1,1-trichloro-3-(m-methoxy)anilinopropan-2-ol.

22. The composition according to claim 2, wherein said compound is N,N-di-(3,3,3-trichloro-2-hydroxypropyl)-aniline.

23. The composition according to claim 2, wherein said compound is 1-p-chlorophenacyl-2-hydroxy-3-trichloropropane.

24. The composition according to claim 2 wherein said compound is 1-p-chlorophenyl-1,3-dihydroxy-4,4,4-trichlorobutane.

25. The composition according to claim 2, wherein said compound is 1-p-chlorophenacyl-3,3,3-trichloroprop-1-ene.

* * * * *